United States Patent [19]

Anstadt

[11] Patent Number: 5,119,804
[45] Date of Patent: Jun. 9, 1992

[54] HEART MASSAGE APPARATUS

[76] Inventor: George L. Anstadt, 6495 E. Agenbroad Rd., Tipp City, Ohio 45371

[21] Appl. No.: 615,214

[22] Filed: Nov. 19, 1990

[51] Int. Cl.$^5$ ............................................. A61H 7/00
[52] U.S. Cl. ........................... 128/64; 128/24 R; 128/38; 128/24.2
[58] Field of Search ............... 128/64, 38, 39, 40, 128/24 R, 24.2

[56] References Cited

U.S. PATENT DOCUMENTS

| | | |
|---|---|---|
| 2,826,193 | 3/1958 | Vineberg . |
| 3,034,501 | 5/1962 | Hewson . |
| 3,053,249 | 9/1962 | Smith . |
| 3,233,607 | 2/1966 | Bolie . |
| 3,279,464 | 10/1966 | Kline . |
| 3,371,662 | 3/1968 | Heid et al. . |
| 3,376,863 | 4/1968 | Kolobow et al. . |
| 3,455,298 | 7/1969 | Anstadt . |
| 3,478,737 | 11/1969 | Rassman . |
| 3,513,383 | 5/1970 | Sausse . |
| 3,587,567 | 6/1971 | Schiff . |
| 3,590,815 | 7/1971 | Schiff .................... 128/64 |
| 3,613,672 | 10/1971 | Schiff ................. 128/64 X |
| 4,048,990 | 9/1977 | Goetz ..................... 128/64 |
| 4,192,293 | 3/1980 | Asrican ............... 128/64 X |
| 4,506,658 | 3/1985 | Casile . |
| 4,621,617 | 11/1986 | Sharma . |
| 4,731,076 | 3/1988 | Noon et al. . |
| 4,809,684 | 3/1989 | Gardner et al. ........... 128/64 |
| 4,922,893 | 5/1990 | Wright et al. ............ 128/64 |

FOREIGN PATENT DOCUMENTS

2321266  3/1977  France ..................... 128/64

Primary Examiner—Robert A. Hafer
Assistant Examiner—Brian E. Hanlon
Attorney, Agent, or Firm—Rosenthal & Putterman

[57] ABSTRACT

A cardiac massage apparatus and a drive system therefor are disclosed. The massage apparatus comprises a cup having a liner that is connected within the cup at its upper and lower ends. Dimensions defining an optimum cup shape as a function of ventricular length are disclosed wherein the heart remains within the cup when mechanically activated.

18 Claims, 5 Drawing Sheets

HEART MASSAGE APPARATUS

FIELD OF THE INVENTION

This invention relates generally to the field of cardiac assist devices and more particularly, to devices of the type which pump the heart by employing an externally applied force to obtain circulatory support without contacting the blood.

BACKGROUND OF THE INVENTION

It has become common practice in the field of surgery to perform complex, prolonged life-saving surgical procedures on the heart. These procedures may include maintaining the circulation of transplantation candidates and pumping for periods as long as several days by artificial means while a suitable donor heart is sought. Similarly, it is also common practice for the surgeon to manually stimulate the heart to pump. However, this can only be maintained for short time periods on the order of minutes, before the surgeon becomes fatigued.

In response to the above-noted need, alternative methods of pumping or assisting the heart to pump have been developed. For example, heart-lung machines have been developed which actually circulate the blood through a pump and are commonly used in procedures such as coronary artery bypass, valve repair, and transitioning to other blood pumps. The heart-lung machine is deficient as it is virtually impossible to circulate the blood through a pump without causing damage to the blood cells and blood born products which can result in post-surgical complications such as bleeding, thrombi formation, and an increased risk of infection.

In response to the above noted deficiencies, an effort was made to develop methods of pumping the heart which did not require direct contact between the pump and the blood. In general, these devices comprise a device which wraps all or a portion of the heart and applies a mechanical force that squeezes the heart in order to pump blood through it.

These devices have a number of features in common. They usually comprise an outer cup of generally parabolic shape and include a flexible inner membrane, also of a similar parabolic shape which is connected to the outer cup along its periphery so as to create an air space therebetween. The outer cup includes an air inlet/outlet and a vacuum pump is utilized to alternately impose a vacuum and to pressurize the air space. Thus, when the air space is pressurized, the membrane moves away from the outer wall and squeezes the heart, thus pumping blood and when the pressure is reversed, the heart is returned to the normal position, thus allowing blood to flow back into the heart to be pumped on the next cycle.

However, the ventricular actuation cups described above are also not without their inherent drawbacks and deficiencies, as most, if not all of the devices taught in the prior art patents fail to give adequate consideration to the basic fact that there is variability in the size and shape of the human heart. Thus, when these devices are used, they exhibit one or more of a number of deficiencies. For example, if the shape of the heart does not closely conform to the shape of the cup, the ventricles can become dislodged from the cup resulting in trauma to the heart muscle and inefficient pumping of the ventricle which is exacerbated the longer the cup is used. Also, if the lip, or flange, of the cup which maintains the seal is "constricting" or "too tight", this can result in trauma to the heart in areas of constriction. Similarly, prior art devices utilize inadequately controlled ventricular pumping pressures which do not adequately or reliably empty both chambers of the heart. This frequently results in inadequate blood flow from either ineffective left or right chamber pumping, or pulmonary edema caused by ineffective pumping of the left chamber or ventricle thereby allowing blood to accumulate in the lungs.

With the foregoing in mind, it is an object of the present invention to provide a heart massage apparatus that reliably and efficiently pumps the heart muscle.

Another object of the present invention is to provide a heart massage apparatus that effectively retains the heart within the cup.

Still another object of the present invention is to provide a heart massage apparatus that minimizes trauma to the heart muscle while it is being pumped.

Yet another object of the present invention is to provide a heart massage apparatus that substantially eliminates trapping of blood in the lower chambers of the heart or in the lungs.

SUMMARY OF THE INVENTION

These and other objects are achieved by providing an improved cardiac massage cup comprising a cup shaped member of rigid material which is adapted to fit loosely over the lower portion of the heart. A liner of flexible material is contained within the cup shaped member and is connected thereto at its upper end a predetermined distance from the apical section and its lower end is similarly connected to the cup shaped member a second predetermined distance from the basal section, thus leaving the middle part of the liner free from the cup shaped member to form an annular diaphragm which contacts the ventricular surface of the heart.

A first inlet is provided and communicates with the space between the diaphragm and the cup shaped member. The inlet is adapted to receive alternately applied relatively high positive and negative air pressures to provide systolic and diastolic effects on the heart. A second inlet means communicates with the interior of the cup shaped member and is adapted to receive a vacuum for holding the cup shaped member in position on the heart. A first pressure transducer measures the pressure within the space between the liner and the cup shaped member and a second pressure transducer is provided for measuring the vacuum holding the cup shaped member on the heart.

BRIEF DESCRIPTION OF THE DRAWINGS

Some of the features and advantages of the invention having briefly been stated, others will appear from the detailed description which follows, when taken in connection with the accompanying drawings in which—

DETAILED DESCRIPTION OF THE PREFERRED EMBODIMENT

While the present invention will be described more fully hereinafter with reference to the accompanying drawings, in which a particular embodiment is shown, it is to be understood at the outset that persons skilled in the art may modify the invention herein described while still achieving the favorable results of this invention. Accordingly, the description which follows is to be understood as a broad teaching disclosure directed to persons of skill in the appropriate arts and not as limiting upon the present invention.

In the discussion which follows, the detailed description of the preferred embodiment is divided into two sections. In the first section, the cardiac massage cup 20 and the method of selection thereof, are described in detail and the use of the cup 20 in combination with the drive system is described thereafter in the section that follows.

CUP CONFIGURATION

As briefly mentioned, supra, in order for a cardiac massage apparatus to function optimally, a number of variables, including cup shape, applied pressure and applied vacuum, must be properly tuned to a given heart. More particularly, as is known to those skilled in the art of medicine, the human heart is subject to variation depending on a number of factors, including age, sex, general health, and others. The discussion which follows is premised on a heart with ventricular chambers whose long axis are of "normal" size falling within the range of approximately 75 mm to 140 mm.

The ideal cup shape varies only slightly based on heart size; i.e., in the direction of an ellipse formula (more blunted apex) for very large hearts, and more in the direction of a conical shape (more conical apex) for very small hearts (of length about 75 mm). It is, therefore, the intent of the invention to define a standard set of cups from which the surgeon may select the proper cup for a particular heart, based on a single measurement of the ventricular length L of the heart.

Figure 11:
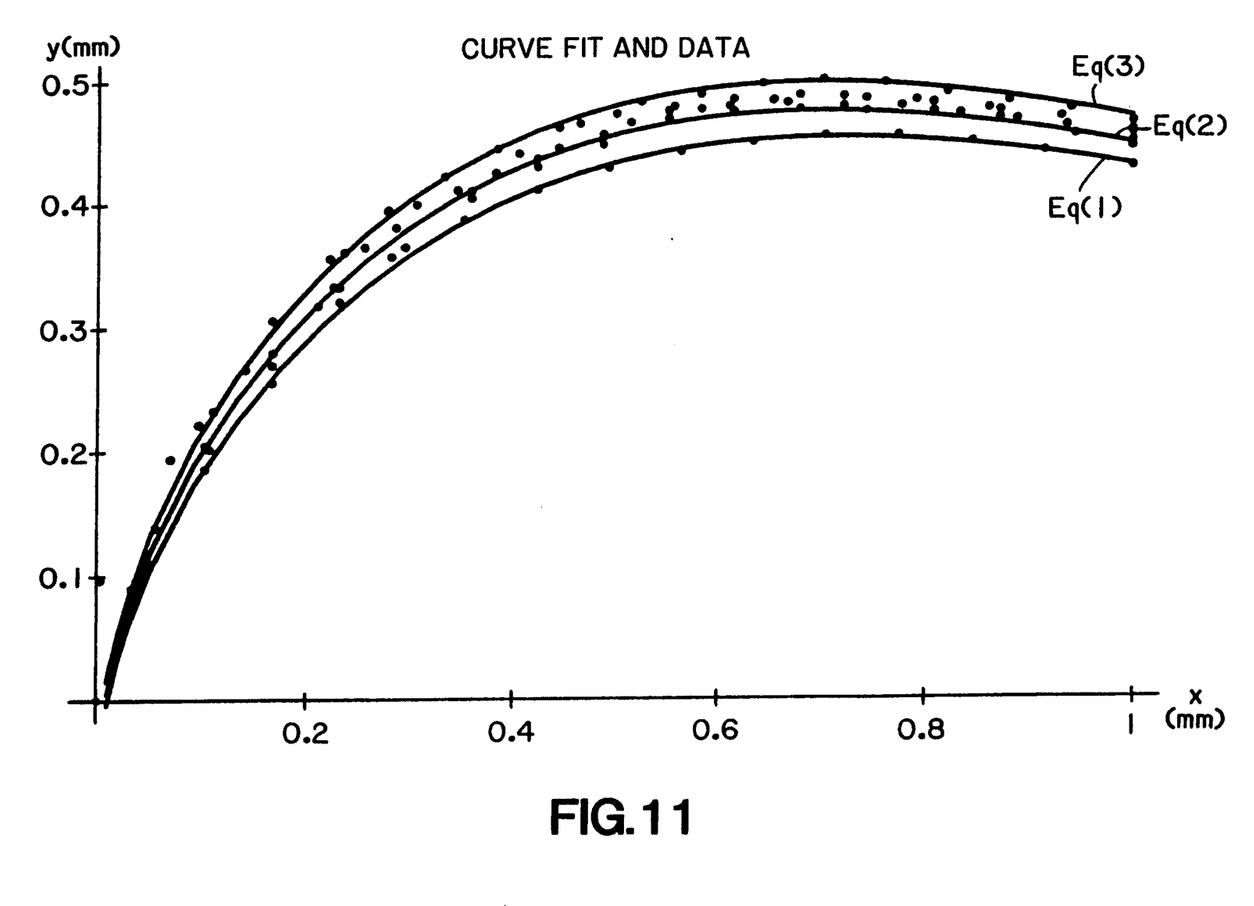
FIG. 11 is a graph representing the cup curvature shape for small, medium and large hearts.

The cup shape for small hearts (75 mm or less) having a ventricular length L is described by equation 1:

$$y = \left[ 0.4542L \sqrt{1.0 - \frac{2.0408(x - 0.7000L)^2}{L^2}} - 0.0846L + 0.3999x - \frac{0.6476x^2}{L} + \frac{0.3516x^3}{L^2} \right] \pm 0.02L \text{ for } 0.075L \leq x \leq L.$$

The cup shape for average hearts (75 mm to 140 mm) having a ventricular length L is described by equation 2:

$$y = \left[ 0.4770L \sqrt{1.0 - \frac{2.0408(x - 0.7000L)^2}{L^2}} - 0.0793L + 0.3987x - \frac{0.6703x^2}{L} + \frac{0.3667x^3}{L^2} \right] \pm 0.02L \text{ for } 0.075L \leq x \leq L.$$

The cup shape for large hearts (greater than 140 mm) having a ventricular length L is described by equation 3:

$$y = \left[ 0.5000L \sqrt{1.0 - \frac{2.0408(x - 0.7000L)^2}{L^2}} - 0.0733L + 0.3897x - \frac{0.6717x^2}{L} + \frac{0.3724x^3}{L^2} \right] \pm 0.02L \text{ for } 0.075L \leq x \leq L.$$

The foregoing relationships are shown graphically in FIG. 11. With the foregoing in mind, reference is now made to FIGS. 4 through 6 which depict the cup in detail. The cardiac massage cup generally indicated at 20 comprises a cup shaped member 30 and a liner 50 of flexible material.

Figure 4:
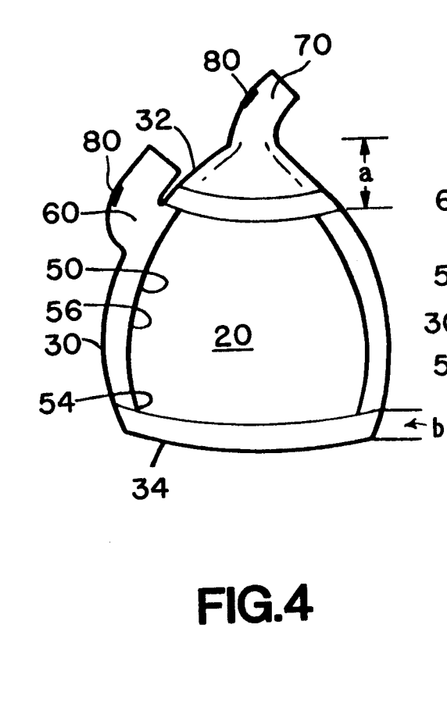
FIG. 4 is a sectional view of the heart massage apparatus of the present invention shown in the diastolic phase.
Figure 5:
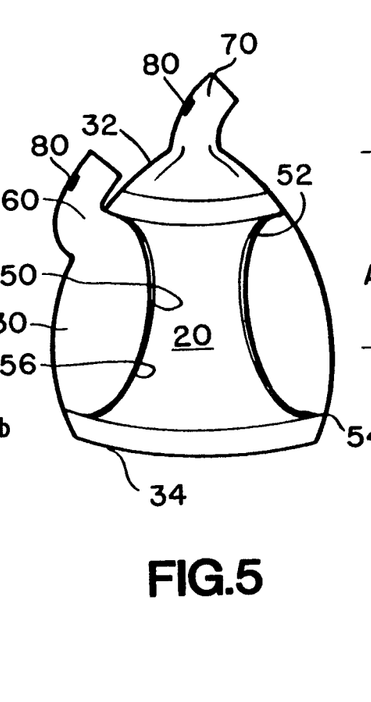
FIG. 5 is a sectional view of the heart massage apparatus of the present invention in the systolic phase.
Figure 6:
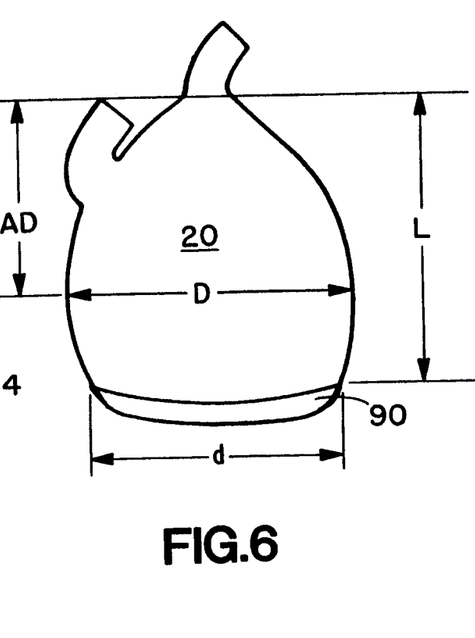
FIG. 6 is a side view of the outer shell or housing of the heart massage of the apparatus of the present invention and showing the flexible flange connected to the basal section of the cup.
Figure 7:
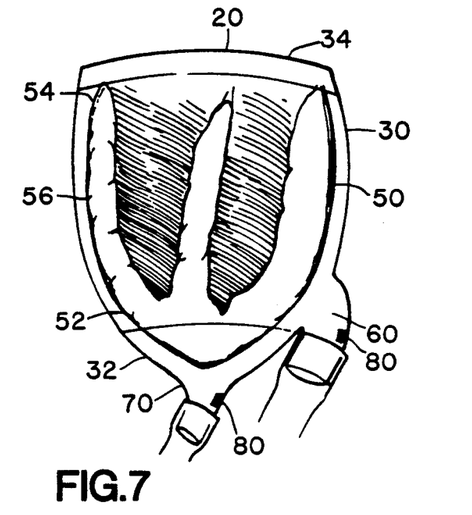
FIG. 7 is a sectional view of the heart massage apparatus of the present invention in place on a heart in the diastolic phase.
Figure 8:
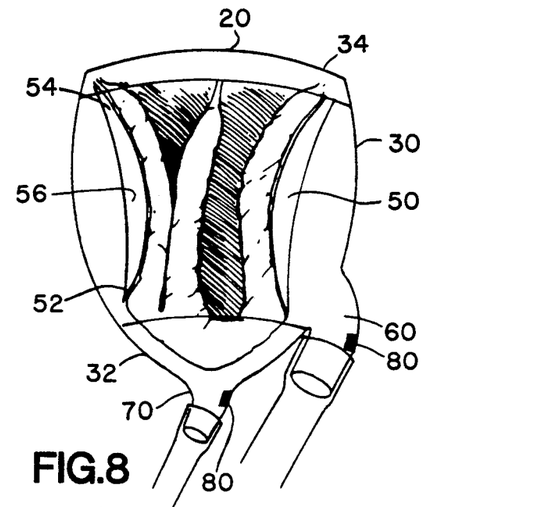
FIG. 8 is a sectional view of the heart massage apparatus of the present invention in place on a heart in the initial portion of the systolic phase.
Figure 9:
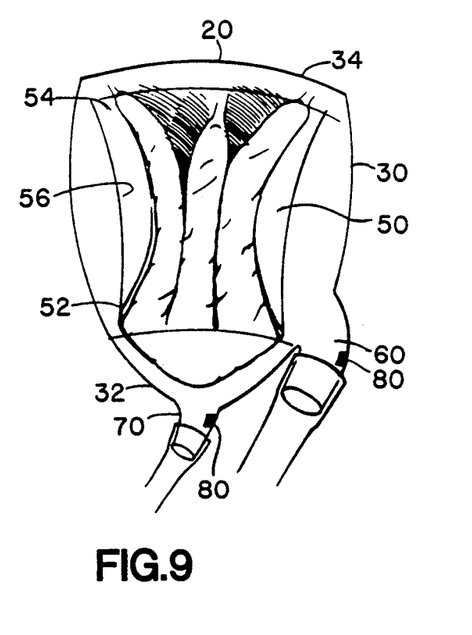
FIG. 9 is a sectional view of the heart massage apparatus of the present invention in place on a heart in the final portion of the systolic phase.
Figure 10:
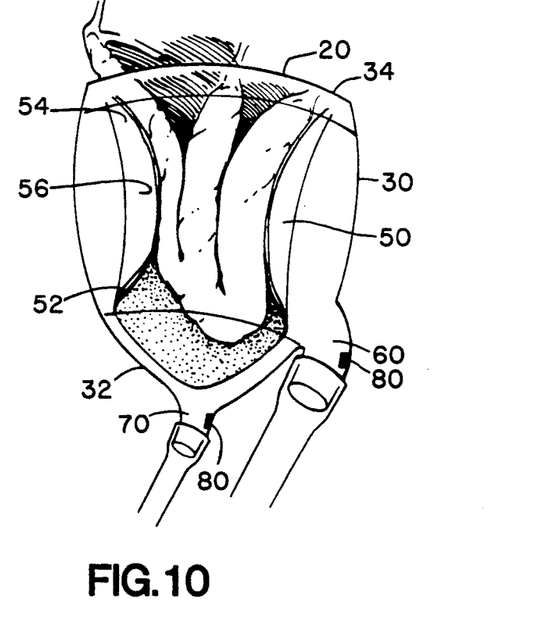
FIG. 10 is a sectional view of the heart massage apparatus according to the prior art wherein the right ventricle has slipped out of the cup shaped member.

The cup shaped member 30 defines a cavity having an apical section and a basal section and is adapted to fit loosely over the lower portion of the heart wherein the apex of the heart is positioned within the cup proximate the apical section 32 of the cup shaped member. Similarly, the basal section or base 34 of the cup extends only as far as the atrial region (i.e., to just below the atrium) of the heart. The cup shaped member 30 has a greatest internal diameter D, an internal basal diameter d, an internal length between the apical section and the basal section L and a dimension AD that defines the distances between the apical section and the greatest internal diameter D. The foregoing parameters are then used to define a cup of optimum shape for a heart of ventricular length L according to the following relationship:

D = 0.96 L +/− 0.05 L
d = 0.90 L +/− 0.05 L
AD = 0.70 L +/− 0.05 L
a = 0.26 L +/− 0.05 L b=0.05 L+/−0.05 L

The cup shaped member 30 is constituted of glass, but could also be an material (preferably translucent) which has adequate rigidity so that it does not collapse during diastolic actuation.

A liner 50 of thin flexible material is contained within the cup shaped member 30 and is connected or bonded thereto with an adhesive such as "Silastic" adhesive at its upper end 52 a distance (a) from the apical section 32. The lower end of the liner 54 is connected to the cup shaped member 30 a distance (b) from the basal section 34 thereof. The lower end of the liner 54 may also be connected at the very end of the basal section 34. Thus, the middle part of the liner 50 is left free from the cup member to form an annular diaphragm 56 which contacts the ventricular surface of the heart. The liner 50 is molded or otherwise prepared out of thin, plastic, translucent material, preferably an air-impervious silicone rubber elastomer such as the material sold by the Dow Corning Company under the trade name "Silastic Q72213". This silicone rubber is widely used in biological applications and is generally recognized to be non-reactive with human tissue. The liner may have a thickness in the range of approximately 0.02 to 0.04 inch. The liner is bonded to the inner surfaces as at (a) and (b) of the cup 30 along its outer edges as shown in FIGS. 4 and 5. The shape of the liner generally follows the curvature of the cup.

The cardiac massage cup also includes a first inlet means 60 adapted to receive alternately applied relatively high positive and negative air pressures to the space between the diaphragm 56 and the cup shaped member to provide systolic and diastolic effects on the heart. In the illustrated embodiment, the first inlet means 60 comprises a hollow side arm adapted to communicate with the pressure system described in detail hereinbelow. The side arm 60 is preferably of material identical to that of the cup shaped member and is fabricated simultaneously therewith. In addition, the side arm is angled toward the apical section 32 of the cup and protrudes a distance less than the maximum external diameter of the cup which assists in maintaining the operating field as small as possible to minimize trauma to the patient.

A second inlet means or second inlet 70 adapted to receive a vacuum for holding the cup shaped member 30 in position on the heart and to communicate with the cavity defined by the cup shaped member is located near the apical end thereof. In addition, transducer means or pressure transducers 80, well known to those skilled in the art are positioned proximate and preferably within each of the first and second inlet means 60, 70 to measure the respective pressures induced therein.

A flange means or flange 90 of flexible material, again such as "Silastic" is connected to the basal section 34 of the cup shaped member and extends around the periphery thereof. The flange 90 tapers in thickness as the distance from the cup increases and is also angled slightly inwardly at about 30 degrees or less toward the heart. The flange assists in maintaining a vacuum seal between the heart and the cup, thus further minimizing the possibility of a ventricle slipping out of the cup.

It will be noted that throughout this specification, the fluid used to actuate the cardiac massage cup is "air". However, other fluids, such as liquid silicone, helium, carbon dioxide, water, or others could be employed with equal efficiency.

Pressure Accessory System

Figure 3:
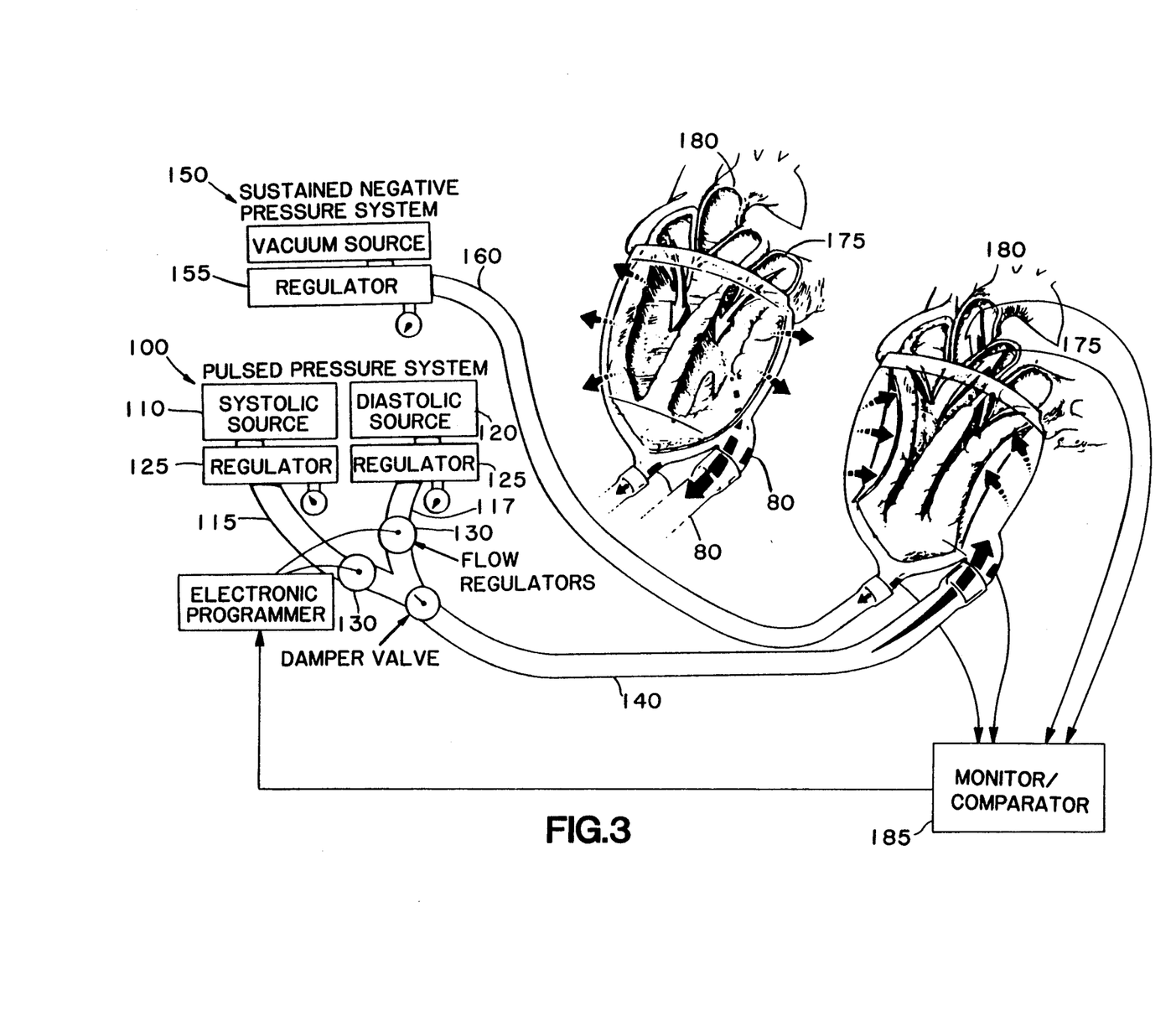
FIG. 3 is a perspective view of the heart massage apparatus of the present invention in place on a heart and illustrating the activation of the apparatus by a schematically shown control apparatus.

FIG. 3 illustrates a pressure and vacuum system in schematic form which can be employed in connection with the improved cardiac massage cup 20. In the figure, reference character 100 designates, in block form, an air pump or pulsed pressure system of any suitable size and well known type and of relatively high flow capacity capable of delivering pressures up to about 200 mm Hg. The air pressure is divided into a systolic source 110 and a diastolic source 120, both of which are regulated using regulators 125 to obtain a peak output in the average region of 120 to 140 mm Hg. The systolic source 100 is output on line 115 and the diastolic source 120 is output on line 117, each of which are electronically controlled, such as with an electronically programmed flow regulator 130 to adjust volume delivery at any instant of the actuating cycle, thereby controlling the liner at any instant of the actuating cycle. The distal end of line 140 is adapted to be pressure fit on to the free end of side arm 60. From the regulated systolic and diastolic sources, the air under regulated pressure, as determined by the particular massaging requirement, is delivered to the space between diaphragm and the cup to control the movement of the liner which in turn massages the heart according to the particular massaging requirement. The forces are adjusted so that low pressures first empty the right ventricle (during the initial 50% of systolic actuation) and then empty the left ventricle in the latter half of systolic actuation. The exact degree of force required to accomplish right ventricle emptying (first half of systolic actuation) and left ventricle emptying (second half of systolic actuation) are precisely delivered by the measurement of the pulmonary artery and systemic arterial pressures in the patient. The drive pressures are then adjusted to match the specific pressures recorded in any given individual. The pulmonary arterial and systemic arterial pressures can be measured by the placement of catheters 175, 180 in the respective pulmonary and systemic arteries as shown in FIG. 3.

The outputs of the pressure transducers 80 from the cup and those from the respective catheters 175, 180 are input to a pressure monitor 185 that monitors the pressures and also produces an output signal that is representative of the difference between the desired pulmonary and systemic arterial pressures. This signal is then fed to an electronic programmer that controls flow regulators 130 to either increase or decrease the output of the pulsed pressure source as needed to maintain the desired blood pressure. Closed loop feedback systems of the type described are well known to those skilled in the art and further discussion thereof is not deemed necessary.

Block 150 generally indicates a vacuum source or pump regulated by regulator 155 for producing a sustained negative pressure. The vacuum is output on line 160 to the second inlet 70 of cup 30 as shown. It is desired that the negative pressure be the least amount that maintains cup attachment (generally less than 80 mm Hg.).

Using the System

Figure 1:
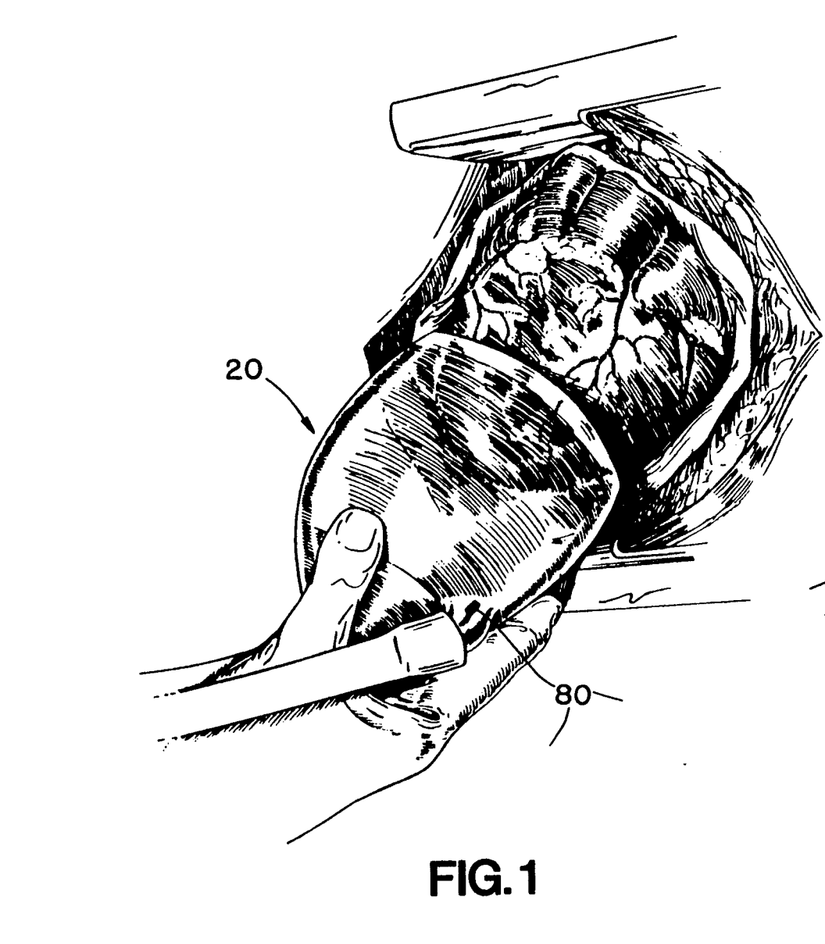
FIG. 1 is a perspective view of the heart massage apparatus of the present invention being inserted over a heart.
Figure 2:
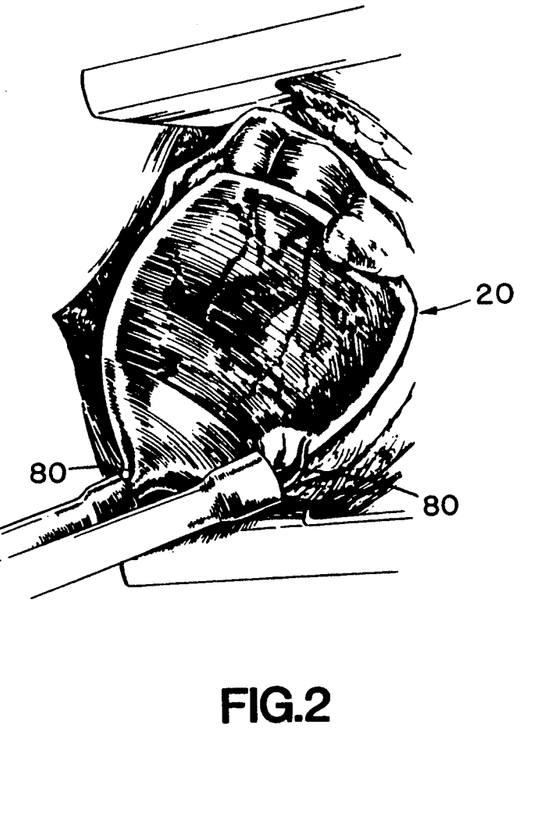
FIG. 2 is a perspective view of a heart massage apparatus of the present invention in place on a heart.

When the surgeon determines that it is necessary to provide mechanical assistance to the heart or to otherwise pump the heart by completely artificial means, the surgeon need only measure the ventricular length L or obtain a visual approximation thereof. A set of cardiac massage cups of varying sizes is provided to the surgeon who selects the proper one from the set for use with a given heart. The cup 20 is then inserted on the heart as shown. It is believed that it is sufficient to provide cups having ventricular lengths ranging from 75 mm to 140 mm in 5 mm increments will be sufficient to satisfactorily fit virtually all the normally encountered hearts.

Once the cup 20 is properly in place on the heart, the negative pressure is activated in line 160. The actual applied pressure is visually adjusted to the minimum which will retain the heart within the cup 20.

Next, the ventricular pressure is applied to the heart ventricles. The goal is to effectively empty the right ventricle (lower force) followed by the left (higher force) followed by dilating the ventricles by applying a negative force to the surface of the heart. This is accomplished by first applying during early systolic compression approximately 25–30 mm Hg. and during late systolic compression approximately 120–150 mm Hg. from systolic source 110. Similarly, during the diastolic phase of each cycle, pressures of approximately −100 to −120 mm Hg. are applied which are adjusted to a greatest negative pressure such that the diaphragm is in continuous contact with the heart.

The pressure measured by the transducer 80 in the side arm of the cup allows drive pressures to be appropriately adjusted to duplicate normal pulmonary and systemic pressures at early and late phases of systolic actuation, respectively. These pressures vary from patient to patient, however, they can easily be obtained from a given individual at the time of cup attachment by use of standard techniques such as pulmonary and arterial catheters.

The use of the described cup transducers is important for proper application of the direct mechanical ventricular actuation concept of the present invention. Since the right ventricle is the first chamber to be emptied by cup actuation, drive pressures must be adjusted so that these actuating forces ar adequate for right ventricular actuation without being overly excessive. If the early forces of systolic compression are to abrupt, the right ventricle will bulge despite optimal cup configuration described above. Finally, the pressures must reach a maximal point which is slightly greater than the patients arterial pressures in late systolic actuation to ensure adequate emptying of the left ventricle. Otherwise, blood will build up in the lungs and pulmonary edema will result.

A single actuation cycle is defined a the moment beginning at the initiation of systolic actuation (positive pressures delivered in drive line 140) to the end of diastolic actuation (end of duration of negative pressure delivered in drive line 140). The cycle is generally divided into halves such that 50% of each cycle is spent in the systolic phase and the remaining 50% is spent in the diastolic phase. The systolic phase of the actuating cycle is adjusted based upon the patient's blood pressure while the diastolic phase is adjusted to ensure that a seal between the liner and the heart is maintained. During the first 50% of the systolic phase, the pressures delivered to the first inlet 60 are adjusted so as not to exceed the patient's measured pulmonary pressures, thereby avoiding right ventricle trauma and slippage. The latter 50% of the systolic phase is then adjusted such that they are no more than 10–20% greater in magnitude than the patient's measured systemic arterial pressure. The diastolic phase of actuation is then adjusted to ensure that the cup maintains a seal with the heart. This is done by gradually increasing the degree of vacuum (i.e., making the pressure more negative) in line 140 to the maximal degree (most negative pressure) where the diaphragm does not separate from the heart. The separation of the diaphragm from the heart is easily detected by observing the constant vacuum pressure measured in the second inlet 70. Any time that this pressure at inlet 70 drops (becomes less negative) indicates the seal between the liner and heart temporarily broke and, therefore, the diastolic actuation was too abrupt at that instant in the diastolic phase.

A transducer 80 in the apical port of the cup allows appropriate vacuums to be utilized for cup attachment. The vacuum for cup attachment is set at the lowest degree of suction that maintains attachment as described above. The loss of attachment is clearly defined by any loss of negative pressure at the cup apex. Once the appropriate vacuum has been determined, continuous suction may be discontinued, and only intermittent suction is applied as needed based on any loss of negative pressure at the apex during actuation.

This tuning is critical to ensure the cup stays attached, particularly during the diastolic, or heart expansion phase. Otherwise, the heart will not be actively dilated and the efficiency of the method will be lost as the heart will dilate more slowly, and ventricular filling will be decreased. This condition will result in decreased cardiac output and hemodynamic deterioration. Also, this tuning will allow the lowest degree of vacuum utilization for cup attachment. Therefore, any trauma that results from use of excessive vacuum is eliminated.

It should be noted that the placement of the transducers within or next to the cup side arm and apical port is critical for the above objectives. Pressure transducers located anywhere else in the system do not measure real-time absolute pressures which are actuating the cup. Any change in drive line length, cup size or drive line connectors will change the relationship between pressures measured at the drive system and those that are directly acting on the cup and heart.

The foregoing embodiments and examples are to be considered illustrative, rather than restrictive of the invention, and those modifications which come within the meaning and range of equivalence of the claims are to be included therein. Furthermore, the terms massage and actuate are used interchangeably to describe the pumping of the heart by mechanical means employing the cup of the present invention for various time periods ranging from short term (minutes) to indefinite (years).

That which is claimed is:

1. A direct mechanical ventricular cardiac massage apparatus comprising:
   a cup shaped member defining a cavity having an apical section and a basal section, said cup shaped member having a greatest internal diameter (D) and an internal basal diameter (d), an internal length between the apical section and the basal section (L) and wherein the dimension (AD) defines distances between the apical section and the greatest internal diameter (D);
   a liner of thin flexible material contained within said cup shaped member and being connected to said cup shaped member at its upper end a distance (a) from the apical section of said cup shaped member and wherein the lower end of said liner is connected to said cup shaped member a distance (b)

from the basal section of said cup shaped member, the middle part of the liner being left free from said cup shaped member and forming an annular diaphragm;

means for alternately applying to the space between the diaphragm and the cup shaped member relatively high positive and negative fluid pressures and; means including a vacuum for holding the cup shaped member in a predetermined position;

said cup shaped member being defined by the relationship:
$D = 0.96\,L +/- 0.05\,L$
$d = 0.90\,L +/- 0.05\,L$
$AD = 0.70\,L +/- 0.05\,L$
$a = 0.26\,L +/- 0.05\,L$
$b = 0.05\,L +/- 0.05\,L$ whereby when the cup shaped member is placed loosely over the lower portion of the heart so that the apex of the heart is positioned within the cup shaped member proximate the apical section thereof and the basal section of the cup shaped member extends only so far as the atrial region of the heart, and the middle portion of the liner that forms the annular diaphragm that contacts the ventricular surface of the heart, and wherein the means for alternately applying to the space between the diaphragm and the cup shaped member transfers pressure to the ventricular surface of the heart to provide systolic and diastolic effects on the heart, and the means including a vacuum holds the cup shaped member in position on the heart the optimum shape of the apparatus is defined for a heart of ventricular length (L).

2. A cardiac massage apparatus according to claim 1 and in which said means for holding the cup shaped member in position includes a vacuum source, and passageways extending from said source to the apical section and the interior of said cup shaped member.

3. A cardiac massage apparatus according to claim 1 and in which said means for alternately applying the relatively high positive and negative fluid pressure include a first inlet means in said cup shaped member at the position of said diaphragm through which said fluid pressure are introduced and a second inlet means proximate the apical portion of said cup through which the vacuum for holding the cup shaped member in a predetermined position is introduced.

4. A cardiac massage apparatus according to claim 1 and in which said means for alternatively applying the positive and negative fluid pressures is constituted of reservoirs of the high and low pressure controlled through a valve apparatus having moving parts for controlling the fluid through the valve, and means including a timing device operated according to a predetermined time sequence for operating the movable parts of the valve in order to control the application of these relatively high and low fluid pressures to the diaphragm.

5. A heart massage apparatus according to claim 3 wherein said cup shaped member is constituted of a semi-rigid material and wherein said first inlet means comprises a side arm extension into which said fluid pressures are introduced against said diaphragm.

6. A heart massage apparatus according to claim 5 wherein said side arm is angled toward said apical section and protrudes a distance that is less than the maximum external diameter of said cup shaped member.

7. A heart massage apparatus according to claim 1 further including a flexible flange means connected to the basal section of said cup shaped member and extending around the periphery thereof.

8. A heart massage apparatus according to claim 7 and in which said flange means is tapered away from the cup shaped member and is angled toward said cavity.

9. A heart massage apparatus according to claim 7 and in which said flange means is parallel to the cup base and is angled toward said cavity.

10. A heart massage apparatus according to claim 7 and in which the angle of orientation of said flange means is less than about 30 degrees toward said cavity.

11. A heart massage apparatus according to claim 3 further including a first pressure transducer means and a second pressure transducer means for measuring the applied pressure positioned respectively within said opening in said cup shaped member at the position of said diaphragm and within said second opening proximate the apical portion of said cup.

12. A heart massage apparatus according to claim 1 and in which the cup shaped member is constituted of a semi-rigid material.

13. A direct mechanical ventricular cardiac massage cup and comprising:

a cup shaped member defining a cavity having an apical section and a basal section, said cup shaped member having a greatest internal diameter (D) and an internal basal diameter (d), an internal length between the apical section and the basal section (L) and wherein the dimension (AD) defines the distance between the apical section and the greatest internal distance (D);

a liner of thin flexible material contained within said member and being connected to said cup shaped member at its upper end a distance a from the apical section of said cup shaped member and wherein the lower end of said liner is connected to said cup shaped member a distance from the basal section of said cup shaped member, whereby the middle part of the liner is left free from said cup member to form an annular diaphragm;

first inlet means adapted to receive relatively high positive and negative fluid pressures applied to the space between the diaphragm and the cup shaped member and;

second inlet means adapted to receive a vacuum for holding the cup shaped member in a predetermined position, said cup shaped member being defined by the relationship:
$D = 0.96\,L +/- 0.05\,L$
$d = 0.90\,L +/- 0.05\,L$
$AD = 0.70\,L +/- 0.05\,L$
$a = 0.26\,L +/- 0.05\,L$
$b = 0.05\,L +/- 0.05\,L$ whereby when the cup shaped member is placed loosely over the lower portion of the heart so that the apex of the heart is positioned within the cup shaped member proximate the apical section thereof and the basal section of the cup shaped member extends only so far as the atrial region of the heart, and the middle portion of the liner that forms the annular diaphragm that contacts the ventricular surface of the heart, and wherein the means for alternately applying to the space between the diaphragm and the cup shaped member transfers pressure to the ventricular surface of the heart to provide systolic and diastolic effects on the heart, and the means including a vacuum holds the cup shaped member in position on the heart the optimum shape of the apparatus is defined for a heart of ventricular length (L).

14. A method of provided cardiac massage using a cup shaped member defining a cavity having an apical section and a basal section which is adapted to fit loosely over the heart, the cup shaped member having a greatest internal diameter (D), an internal basal diameter (d), an internal length between the apical section and the basal section (L), and wherein the dimension (AD) defines the distance between the apical section and the greatest internal diameter (D) and a liner of thin flexible material contained within the cup and being connected to the cup shaped member at its respective upper and lower ends, the middle part of the liner being left free from the cup shaped member to form an annular diaphragm which is adapted to contact the ventricular surface of the heart, and wherein a system is provided for alternately providing to the space between the liner and the cup shaped member a relatively positive fluid pressure and a negative fluid pressure and a vacuum system for holding the cup shaped member in position on the heart and comprising the steps of:

measuring the ventricular length (L) of the heart to be mechanically supported;

selecting from a preselected set of cups, the cup most nearly satisfying the relationship:
    D=0.96 L+/−0.05 L
    d=0.90 L+/−0.05 L
    AD=0.70 L+/−0.05 L
    a=0.26 L+/−0.05 L
    b=0.05 L+/−0.05 L     inserting the selected cup shaped member into the body cavity;

positioning the selected cup shaped member over the heart;

applying a vacuum to the selected cup shaped member to maintain the cup shaped member in position on the heart;

applying alternately to the space between the liner and the selected cup shaped member a relatively positive fluid pressure and a negative fluid pressure;

measuring the vacuum and the alternating relative positive fluid pressure and the negative fluid pressure;

adjusting the vacuum and the alternating relative positive fluid pressure and the negative fluid pressure to maintain the heart within the selected cup and to pump blood through the heart.

15. A method of mechanically pumping a human heart by determining the optimum shape of a direct mechanical ventricular actuation cup of the type having a cup shaped member defining a cavity having an apical section and a basal section,     a liner of thin flexible material positioned within the cavity having one end connected proximate the apical section and its other end of the liner connected proximate the basal section of the cup, the middle part of the liner being left free from the cup and forming an annular diaphragm; and further including a first inlet communicating with the space between the diaphragm and the cup and a second inlet communicating with the chamber comprising the steps of:

(a) measuring the ventricular length (L) of the heart to be mechanically supported;

(b) selecting a cup having the shape:

(i) for (L) less than 75 mm:

$$y = \left[ 0.4542L \sqrt{1.0 - \frac{2.0408(x - 0.7000L)^2}{L^2}} - 0.0846L + 0.3999x - \frac{0.6476x^2}{L} + \frac{0.3516x^3}{L^2} \right] \pm 0.02L$$

(ii) for (L) between 75 to 140 mm:

$$y = \left[ 0.4770L \sqrt{1.0 - \frac{2.0408(x - 0.7000L)^2}{L^2}} - 0.0793L + 0.3987x - \frac{0.6703x^2}{L} + \frac{0.3667x^3}{L^2} \right] \pm 0.02L$$

(iii) for (L) greater than 140 mm:

$$y = \left[ 0.5000L \sqrt{1.0 - \frac{2.0408(x - 0.7000L)^2}{L^2}} - 0.0733L + 0.3897x - \frac{0.6717x^2}{L} + \frac{0.3724x^3}{L^2} \right] \pm 0.02L$$

(c) placing the cup on the heart so that the apex of the heart is positioned proximate the apical section and the basal section extends only as far as the atrial region of the heart;

(d) applying alternately to the first inlet a relatively positive fluid pressure and a negative fluid pressure.

16. The method according to claim 15 further including the step of feeding back to a control unit a signal representative of the measured vacuum and a signal representative of the alternating relative positive fluid pressure and the negative fluid pressure.

17. The method according to claim 16 further including the step of utilizing the signal representative of the measured vacuum and a signal representative of the alternating relative positive fluid pressure and the negative fluid pressure to precisely measure and control the vacuum and the pressure.

18. The method of mechanically pumping a human heart according to claim 15 further including the step of applying to the second inlet a vacuum to hold the cup on the heart.

* * * * *